United States Patent [19]
Asselain et al.

[11] Patent Number: 5,453,619
[45] Date of Patent: Sep. 26, 1995

[54] METHOD AND APPARATUS FOR THE SPECTROPHOTOMETRIC ASSAY OF AQUEOUS LIQUIDS

[76] Inventors: Marc Asselain, 193, rue du Bosquet, F-34980 Saint-Gely; Daniel Manifacier, Les Bonbelles, F-30500 Saint-Ambroix; Yves Agnet, 1985, rue de Saint-Paul, F-30129 Manduel, all of France

[21] Appl. No.: 150,192

[22] Filed: Dec. 8, 1993

[30] Foreign Application Priority Data

Jun. 10, 1991 [FR] France .................... 91 07116

[51] Int. Cl.⁶ .......................... G01N 21/25; G01N 21/35
[52] U.S. Cl. ................... 250/339.12; 250/339.03; 250/339.04; 250/343; 250/910
[58] Field of Search ............. 250/339.07, 339.08, 250/339.12, 339.03, 339.04, 343, 910

[56] References Cited

U.S. PATENT DOCUMENTS

| | | |
|---|---|---|
| 4,825,076 | 4/1989 | Shields. |
| 4,963,743 | 10/1990 | Satake et al. .............. 250/339.07 |
| 5,091,649 | 2/1992 | Rantala ................. 250/339.13 X |
| 5,252,829 | 10/1993 | Nygaard et al. ............ 250/343 X |
| 5,258,620 | 11/1993 | Sueyasu et al. ............ 250/343 X |

FOREIGN PATENT DOCUMENTS

| | | |
|---|---|---|
| 0404207 | 12/1990 | European Pat. Off. . |
| 61-65122 | 4/1986 | Japan ................. 250/339.08 |
| 1133551 | 1/1985 | U.S.S.R. ............... 250/910 |

OTHER PUBLICATIONS

Fuller, et al., "Partial Least–Square Quantitative Analysis of Infrared Spectroscopic Data. Part I: Algorithm Implementation", *Applied Spectroscopy*, vol. 42, No. 2 (1988), pp. 217–227.

Primary Examiner—Carolyn E. Fields
Assistant Examiner—Edward J. Glick
Attorney, Agent, or Firm—Sandler, Greenblum & Bernstein

[57] ABSTRACT

Method and apparatus for the spectrophotometric assay of aqueous liquids are provided with a pump for aspirating liquids, a filter with two outlets for filling a cell in which the interferometric measurements are made at a temperature between 35 and 50° C. at a maximum fluctuation of 0.2° C., and with a maximum relative humidity of 0.2%. Absorption curves $A(f)$ are determined with respect to a matrix and the concentrations of components to be assayed are calculated by the use of standard equations.

23 Claims, 3 Drawing Sheets

METHOD AND APPARATUS FOR THE SPECTROPHOTOMETRIC ASSAY OF AQUEOUS LIQUIDS

BACKGROUND OF THE INVENTION

1. Field of the Invention

The present application concerns a method and apparatus for the assay of aqueous liquids containing components to determine their concentration.

2. Discussion of Background Information

Assays of aqueous liquids are undertaken by spectrophotometry in an infrared range of which the wavelength is from 2 to 25 μm.

The main problem for this type of assay is that the water absorption of the infrared radiation in the band indicated (2 to 25 μm) is substantial.

If the intensity of a radiation beam transmitted through a cell filled with water is (Io), and that through a cell filled with aqueous liquid to be assayed is (I), then the absorbency of the components is Log Io/I.

In order to obtain exploitable measurements, the difference between the signal corresponding to the radiation transmitted by a cell filled with liquid to be assayed and that corresponding to the radiation transmitted by the same cell filled with water must be large in proportion to the noise mixed with the measurements taken.

This requires adjustment of the intensity of the incident radiation for each wavelength, or more precisely, for each band of the spectrum corresponding to a function (connection) to be inspected of the components in question.

The adjustment of each band is necessary because, for a polychromatic beam, the energy corresponding to each wavelength is not equal, therefore, such adjustment allows a quantity of energy, for which the signal/noise ratio for the utilized detector is maximum, to pass through the cell.

The intensity adjustment of each band enables one single detector to be used for all the bands, one after another, while working in a sensor area where the signal/noise ratio is high.

Currently, the quantitative analysis by spectrophotometry in an aqueous medium is undertaken by means of monochromatic beams of which the intensity is adjusted.

The word "monochromatic", here means a frequency band whose width is narrow. This is obtainable by means of a polychromatic source cooperating with several optical filters; each one selects and adjusts (attenuates more or less) the intensity of a frequency band such that the energy transmitted for each band corresponds to the sensor area in which the signal/noise ratio is adequately high, in other words, such that the signals measured are exploitable.

Therefore, spectrophotometric quantitative analysis systems in an aqueous medium are dispersive systems. Several monochromatic beams are used; each is obtained from the same polychromatic source and an appropriate filter.

The disadvantages of such systems are:

The number of bands to be inspected corresponds to a number equal to or less than that of the filters; in order to have a spectrum covering the entire range of bands, a very large number of filters is necessary.

The slowness, because the necessary measurements must be undertaken for each band (each filter). In addition, between two successive measurements, it is necessary to wait until the optical and mechanical stability of the system is reached, in other words, one must wait until the mechanical vibrations engendered by the motion involved in changing filters are damped.

Indeed, in order for these dispersive systems to have an acceptable rate, it is necessary to limit the number of bands to be inspected; this number is currently from 1 to 4 bands for each sample.

The number of samples to be analyzed for the fastest systems is on the order of 300 samples per hour.

Non-dispersive spectrophotometric analysis systems, that is, interferometric systems, are currently used either for qualitative analyses or approximate quantitative analyses for samples where the absorption frequencies of the components are distant from the absorption frequencies of the liquid matrix. The matrix may be a solvent or, in a general manner, the liquid containing the components.

These systems are not currently utilizable for quantitative analyses, especially in the case where the components to be quantified and the matrix absorb the same or very closely related radiation.

The advantage of these systems is speed, because an interferogram involving the entire frequency range is obtained in a single series of measurements.

This interferogram, with the aid of another interferogram corresponding to the matrix, enables the absorbance spectrum to be determined for all the wavelengths of the frequency range.

The major disadvantage of these systems is that a quantitative analysis is not possible in a liquid medium where the matrix and the components to be detected absorb radiation of the same frequency; this is typical in the case of milk for the assay of fats, proteins and lactose.

Indeed, spectrophotometric analysis by interferometry is reputedly impossible for the assay of milk components.

SUMMARY OF THE INVENTION

Contrary to the accepted idea that certain liquid medium cannot be quantitatively analyzed where the matrix and the components to be detected absorb radiation of the same frequency, the present invention renders possible the assay of milk components, for example, by interferometry with an uncertainty of less than 0.6 g/kg for each component and a repeatability of which the fluctuation is less than 0.18 g/kg for each component, provided that certain predetermined physical parameters are respected during the measurements.

The object of the present invention is thus to propose a method and apparatus for quantitative analyses by interferometry in an aqueous medium for a spectrum whose wavelength runs from 2 to 25 μm.

Another object of the invention is to propose an assaying apparatus, the rate of which can attain 800 samples per hour, regardless of the number of components to be assayed.

Yet another object of the present invention is to enable a complete absorption spectrum to be obtained for the totality of the components; this is very interesting for several reasons such as, for example:

to enable all the bands of the spectrum concerning a given component to be taken into consideration, either for a same connection in order to perfect the result to be obtained by introducing the maximum correlation coefficients regarding the connection concerned, or for two or more different connections regarding the same component, to enable the absorption spectrum to be explored at will for the assay of other components present in the sample; this may lead to more complete analyses.

Currently, dispersive spectrophotometric analysis systems allow the exploration of only a limited number of predetermined frequency bands. This necessarily limits the number of components to be assayed, and limits research into the influence of all the components on the absorption behavior for a given component in a given band.

To this end, the method included in the present invention for the spectrophotometric assay of aqueous liquids containing components $X_1, X_2, \ldots, X_n, \ldots$, in order to determine their concentration $C_1, C_2, \ldots, C_n, \ldots$, for an infrared spectrum of which the wavelength is from 2 to 25 μm, is characterized substantially in that it comprises the following steps:

1/ Sampling at least one water interferogram for the entirety of the predesignated wavelengths, through a water thickness of 10 to 20 μm, such sampling to be undertaken by respecting the following conditions:
   a—temperature: 35° to 50° C.,
   b—maximum fluctuation in temperature: 0.2° C.,
   c—maximum relative hygrometry: 1%.

2/ Calculating, from the water interferogram, the spectrum (So(f)) corresponding to the intensity (Io) traversing said water thickness as a function of the frequency (f), (So) being the measured values.

3/ Sampling at least one interferogram of said liquid, for the same thickness and under the same conditions as in step 1.

4/ Calculating the spectrum (S(f)), corresponding to the intensity (I) traversing the liquid thickness according to the frequency (f).

5/ Determining, from (So(f)) and (S(f)), the absorbance (A(f)), given A(f)=Log (So/S)=Log (Io/I).

6/ Determining the concentration of each of the components concerned, from the absorbance (A(f)) and by means of the chosen reference analyses.

In another characteristic of the method, the concentration $C_n$ of each component $X_n$ is determined by taking into consideration several absorbencies $A(f_1), A(f_2), \ldots, A(f_r)$ according to a standard equation of the type:

$$C_n = a_{n1}A(f_1) + a_{n2}A(f_2) + \ldots, A_{nr}A(F_r) + a_{nk}$$

where $A(f_1), A(f_2), \ldots, A(f_r)$ are absorbance values determined for said liquid at frequencies $f_1, f_2, \ldots, f_r$ and, $a_{n1}, a_{n2}, \ldots, a_{nr}, a_{nK}$ are correlation coefficients determined by multiple linear regression based on reference samples with known concentrations and interferometric measurements undertaken on the same samples and corresponding to the same frequencies $f_1, f_2, \ldots, f_r$.

In yet another characteristic of the method, the sampling of each interferogram is undertaken at:
   a temperature of 38° to 42° C. of which the maximum fluctuation is 0.1° C.,
   a maximum relative hygrometry of 0.2%.

According to a second arrangement, the apparatus for assaying the liquid, included in the present invention, is characterized substantially in that it comprises:
   an interferometer producing a polychromatic beam interfered with by successive phase shifts obtained around a zero phase shift,
   a measurement container containing:
      a—a means for temperature detection outputting a significant signal transmitted to a calculation and control unit (U.C.C.),
      b—a heating means controlled by the U.C.C. in order to maintain the temperature inside the container at a value between 35° and 50° C. with a maximum fluctuation of 0.2° C.,
      c—a means for limiting the relative humidity at a maximum value of 1%,
      d—a cell of flattened shape with an internal spacing of 10 to 20 μm to be filled with the liquid to be assayed,
      e—a photosensitive detector receiving the interfered beam leaving the cell after traversing it and outputting consistent signals for each phase shift,
   a calculation and control unit receiving, among others, the signals from the photosensitive detector with respect to the phase shifts and calculating:
      a spectrum (S(f)) corresponding to the intensity (I) transmitted as a function of the frequency (f),
      the absorbency A(f)=Log (S°/S)=Log I°/I where S°(f) is a water spectrum corresponding to the intensity (I°) as a function of the frequency (f),
      the concentrations $C_1, C_2, \ldots, C_n, \ldots$, based on the absorbency and by means of chosen reference analyses.

In another characteristic, the apparatus is characterized by three temperature regulation steps:
   a first step constituted by a first heat sensor located in the vicinity of the pump, to detect the temperature ($T_1$,) of the liquid to be introduced into the measurement container outputting a significant signal of said temperature to the U.C.C., and a first heating means controlled by said U.C.C. to maintain the temperature of the liquid intended for analysis at a temperature ($T_1$),
   a second step constituted by a second heat sensor located in the measurement container, to measure its ambient temperature ($T_2$) outputting a thermal signal of said temperature to the U.C.C., and a second heating means controlled by the U.C.C. to maintain the temperature of said ambient environment at a temperature ($T_2$), where $T_2-T_1=0.5°$ C.,
   a third step constituted by a third heat sensor affixed to the cell, to measure its temperature ($T_3$) and outputting a significant signal of said temperature to the U.C.C., and a third heating means controlled by the U.C.C. to maintain said cell at a temperature ($T_3$), where $T_3-T_2=+0.5°$ C., The last two regulation steps constituting the thermal detection means and the heating means for regulating the temperature of the container.

BRIEF DESCRIPTION OF THE DRAWINGS

The invention will be better understood upon reading the following detailed description accompanied by drawings in which.

DETAILED DESCRIPTION OF THE PREFERRED EMBODIMENTS

The process consist substantially of first sampling the interferograms under specific thermic and hygrometric conditions in order to minimize the fluctuations of the measurements due to these two parameters, and then exploiting the maximum of information contained in these measurements so that the calculated concentrations are as close as possible to reality.

The measurement conditions are:

a temperature between 35° and 50° C. and, preferably, between 37° and 45° C., with a maximum fluctuation of 0.2° C., and preferably of 0.1° C., a maximum relative humidity of 1%, and preferably of 0.2

A routine assay has the object of rapidly determining identified components for a series of liquid samples, with an acceptable degree of precision.

This assay consists of sampling an interferogram for a liquid comprising components $X_1, X_2, \ldots, X_n, \ldots$, and then calculating the absorbance of the liquid with respect to the matrix constituting the basis of the liquid, and referring to standard equations concerning each component in order to predict the concentrations $C_1, C_2, \ldots, C_n, \ldots$ Setting up the standard equations for components $X_1, X_2, \ldots, X_n, \ldots$, includes:

undertaking reference analyses on a series of liquid samples comprising the components $X_1, X_2, \ldots, X_n, \ldots$, at variable concentrations.

for each of the liquids, establishing an absorption curve with respect to the frequency A(f), considering the concentration of each constituent to be:

$$C_n = a_{n1}A(f_1) + a_{n2}A(f_2) + \ldots + A_{nr}A(f_r) + A_{nk}$$

where $A(f_1), A(f_2), \ldots, A(f_r)$, are liquid absorbencies at frequencies $f_1, f_2, \ldots, f_r$, by multiple linear regression from the concentrations found by the reference analyses for the liquid samples and the absorbencies determined for the same liquids, calculating the correlation constants $a_{n1}, a_{n2}, \ldots, a_{nr}, a_{nk}$, for each component.

The following is an example for the setting of standard equations for fats (M.G.) of the proteinic material (M.P.) in milk:

TABLE 1

| 1/ REFERENCE ANALYSIS: | | |
|---|---|---|
| SAMPLE | M.G. (mg/kg) | M.P. (mg/kg) |
| 1 | 24.1 | 24.1 |
| 2 | 24.7 | 31.9 |
| 3 | 24.3 | 39.5 |
| 4 | 39.0 | 24.5 |
| 5 | 39.0 | 31.9 |

TABLE 2

| 2/ ABSORBENCY A(f) | | | | |
|---|---|---|---|---|
| Sample | $f_1$ | $f_2$ | $f_3$ | $f_4$ |
| 1 | 0.1596 | 0.1477 | 0.4023 | 0.1668 |
| 2 | 0.1604 | 0.2053 | 0.3936 | 0.1701 |
| 3 | 0.1563 | 0.2629 | 0.3935 | 0.1693 |
| 4 | 0.2664 | 0.1441 | 0.3890 | 0.2458 |
| 5 | 0.2668 | 0.2004 | 0.3846 | 0.2481 |

$f_1 = 1745$ cm$^{-1}$,
$f_2 = 1548$ cm$^{-1}$,
$f_3 = 1040$ cm$^{-1}$,
$f_4 = 2873$ cm$^{-1}$.

3/ CALCULATED STANDARD EQUATIONS $$C(M.G.) = 74.4900\, A(f_1) + 2.0620\, A(f_2) + \quad (1)$$
$$4.3699\, A(f_3) + 88.3947\, A(f_4) + (-4.6602)$$

$$C(M.P.) = 27.4633\, A(f_1) + 136.1743\, A(f_2) + \quad (2)$$
$$13.5142\, A(f_3) + (-24.3837)\, A(f_4) + (-1.8142)$$

4/ Comparison of reference concentrations (C.ref) (Table 1) with the calculated concentrations (C. cal.) of fat (M.G.) and the proteinic material (M.P.) based on the absorbency (Table 2) and the standard equation of each component (Equations 1 and 2, respectively).

TABLE 3

| | M.G. | | M.P. | |
|---|---|---|---|---|
| Sample | C.ref | C.cal | C.ref | C.cal |
| 1 | 24.1 | 24.0 | 24.1 | 24.1 |
| 2 | 24.7 | 24.5 | 31.9 | 31.7 |
| 3 | 24.3 | 24.2 | 39.5 | 39.5 |
| 4 | 39.0 | 38.9 | 24.5 | 24.4 |
| 5 | 39.0 | 39.2 | 31.9 | 31.9 |

This simplified example is given as a guide; the assay may be undertaken for other liquids containing more components, and the determination of the standard equation for each component may be based on the absorbency at a greater number of frequencies.

Figure 1:
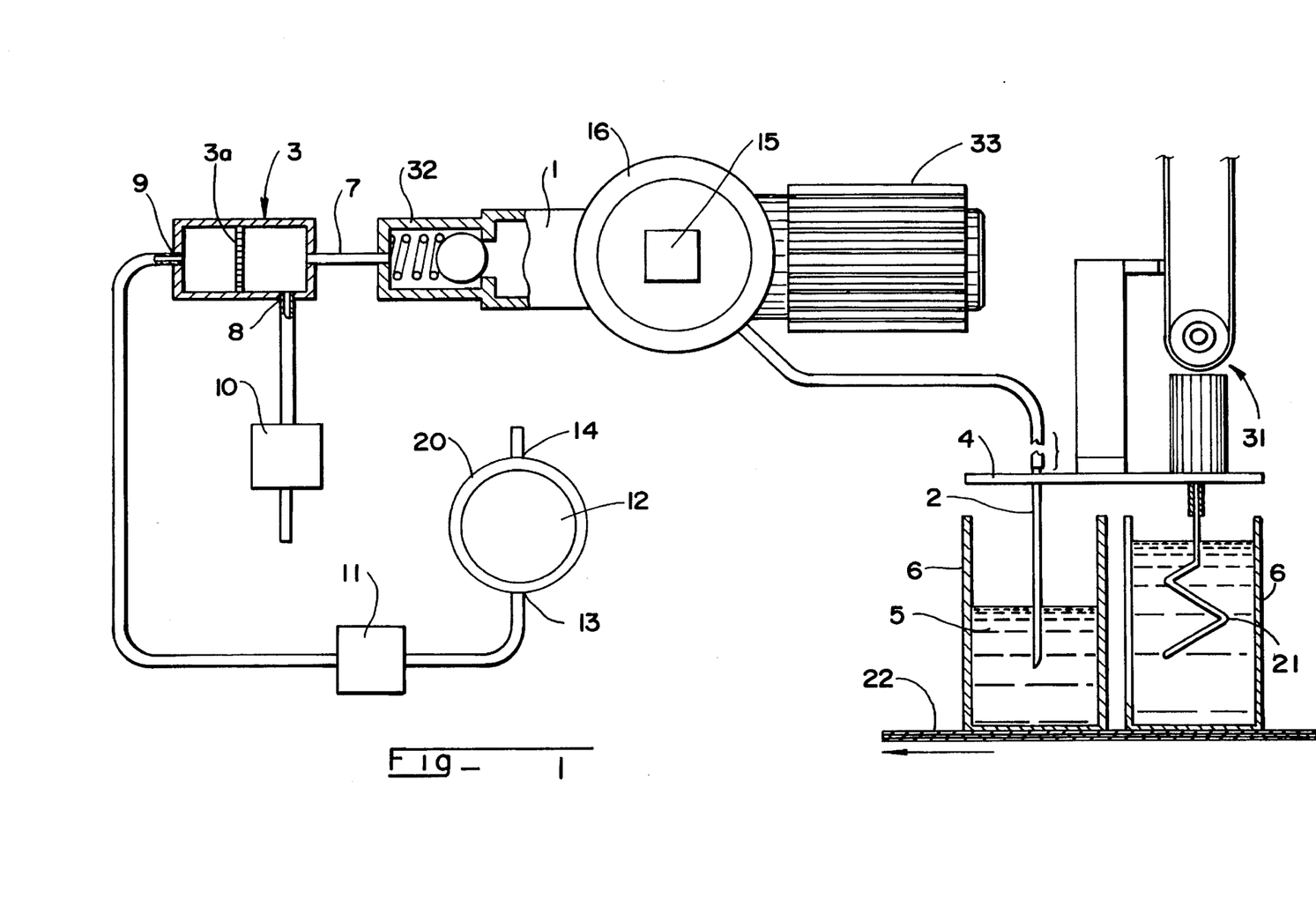
FIG. 1 is a diagram describing the circuit of the liquid in the apparatus.
Figure 2:
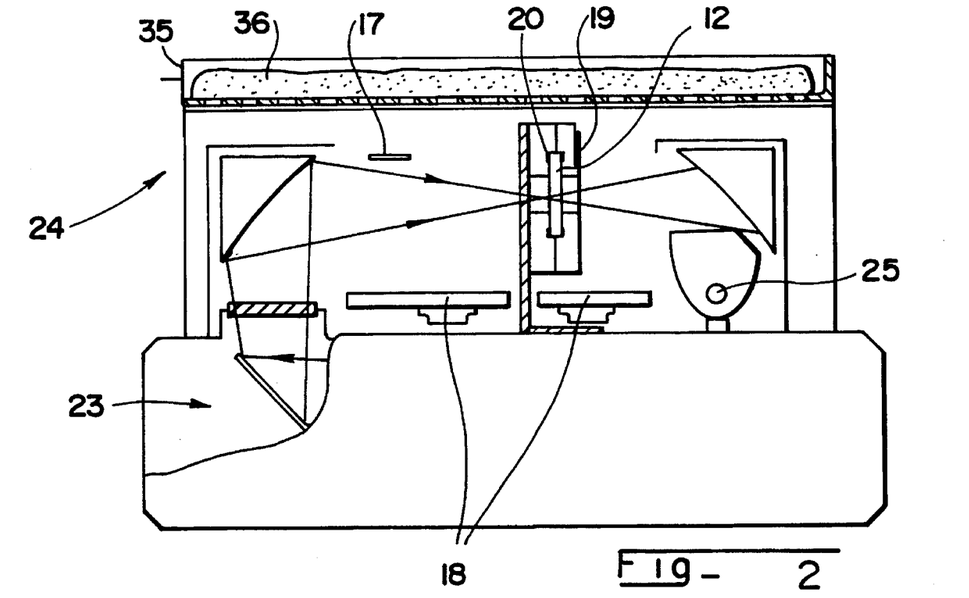
FIG. 2 is a sectional schematic view of the measurement container placed on the interferometer.

In FIGS. 1 and 2, the main elements of the apparatus are illustrated schematically.

A changer 22, such as, for example, an endless band, carries the liquid samples to be assayed, with each liquid 5 being contained in a receptacle 6. The changer cooperates with a presence detector not shown.

The role of this detector is to deliver a signal indicating the presence of the receptacle with respect to a pipette 2; this signal is utilized to control stopping of the band.

The pipette 2 and an agitator 21 are carried by a vertically movable carriage 4 by means of a motive member 31 equipped with transmission means.

The carriage is movable between two positions, i.e., a high position and a low position.

The presence of the agitator is necessary in the case where the liquid to be assayed comprises components having a tendency to separate from the rest of the liquid, either by flotation or by precipitation, as is the case of the fat in milk; agitation is therefore necessary in order for the assayed liquid to be representative.

In the case where the carriage carries an agitator, the pipette - agitator spacing is identical to the spacing between two successive receptacles; this enables the agitation of a receptacle during the aspiration of the liquid contained in the preceding receptacle.

A pump 1 aspirates the liquid from the receptacle. This pump is a diaphragm pump whose mechanical portion is provided with a cooling radiator 33.

The pump utilized is a four-cycle/second pump producing an approximate pressure of 190 to 200 bars during the lift; the portion of the pump containing the liquid is equipped with a heating means such as, for example, a heating belt 16 and a heat sensor 15.

The outlet of the pump is connected to a conventional ball homogenizer 32 with an approximate resistance of 180 bars. The residual pressure at the homogenizer outlet, is approximately 10 to 15 bars.

The role of the homogenizer is to divide certain components in order to reach a size of approximately 1 μm and as a result to avoid the phenomenon of optical diffraction of the beam (wavelength 2 to 25 μm).

Upon exiting the pump, the liquid is directed in a filter 3 having a filter element 3a, an inlet 7 and two outlets 8 and 9. The outlet 8 is controlled by a valve 10 which is normally open and leading towards a recovery receptacle or towards a drain channel not shown. The outlet 9 is controlled by a valve 11 and leads towards a cell 12.

Cell 12 has a flattened shape and an internal spacing of 10 and 20 μm, and preferably 15 and 18 μm; the cell has an inlet 13 located at its lowest level and an outlet 14 located at its highest level. The outlet of the cell leads to a recovery receptacle or a drain channel not shown.

This cell is located in a measurement container 24 associated with an interferometer 23.

The interferometer produces a polychromatic beam interfered with by successive phase shifts taken around a zero phase shift position.

The monochromatic components of the polychromatic beam have wavelengths ranging from 2 and 25 μm, i.e., frequencies of 400 to 5,000 cm−1.

The cell is equipped with a heating means such as, for example, a heating belt 20 whose control is established based on a signal from a heat sensor 19 affixed to the cell; this concerns the temperature regulation of the liquid in the cell.

The container is equipped with a heat sensor 17 located upstream from the cell, and a heating means such as, for example, a heating block 18 to regulate the ambient temperature and accordingly, the passage of the beam.

The container is equipped with a means for reducing the relative humidity to a maximum value of 1%, preferably of 0.2%. Such means consists of a drawer (35) in which a bag with permeable walls is filled with a solid desiccation agent (silica gel or equivalent).

The wall 37 between the drawer and the container is permeable.

The interfered polychromatic beam traverses the cell in order to be detected by a photosensitive detector 25.

The detector 25 outputs signals (voltages) corresponding to each phase shift.

The apparatus is equipped with a calculation and control unit 30 (U.C.C.) receiving, among others, the signals output by the detector 25 as a function of each phase shift and calculating:

by rapid Fourrier Transform (TF), a spectrum (S(f)) corresponding to the light intensity (I) (infrared polychromatic beam) received, where (f) is the frequency, the absorbency A=Log (So/S)=Log (Io/I), where (Io) is the light intensity received for a cell filled with water.

The thermal regulation of the apparatus is obtained by three steps:

a first step constituted by a first heat sensor located in the vicinity of the pump, for detecting the temperature ($T_1$,) of the liquid to be introduced into the measurement container, outputting a significant signal of the temperature to the U.C.C., and a first heating means controlled by the U.C.C. to maintain the temperature of the liquid intended for the analysis at a temperature ($T_1$), a second step constituted by a second heat sensor located in the measurement container measuring its ambient temperature ($T_2$,) outputting a thermal signal of the temperature to the U.C.C., and a second heating means controlled by the U.C.C. to maintain the temperature of the ambient environment at a temperature ($T_2$), where $T_2-T_1=0.5°$ C., a third step constituted by a third heat sensor affixed to the cell for measuring its temperature ($T_3$,) and outputting a significant signal of the temperature to the U.C.C., and a third heating means controlled by the U.C.C. in order to maintain the cell temperature at ($T_3$), where $T_3-T_2=+0.5°$ C., The last two regulation steps constituting the heat detection means and the heating means for regulating the container temperature.

The first heating means can be constituted by a heating collar 16 cooperating via the U.C.C. with the first heat sensor 15 located on the portion of the pump including the liquid to be introduced into the measurement container.

The second heating means can be constituted by a heating block 18 located on the base of the container, cooperating with a heat sensor 17 located in the atmosphere of the container, and preferably downstream from the cell.

The third heating means can be constituted by a heating belt 20 surrounding the contour of the cell cooperating with a heat sensor 19.

It must be noted that heat sensors 15, 17 and 19 must be capable of measuring the temperature with an uncertainty of 0.1° C.

Sensors that meet these precision requirements are available on the market.

It should also be noted that the heating means may have other known forms.

Furthermore, the number of thermal regulation steps may be greater than three.

Figure 4:
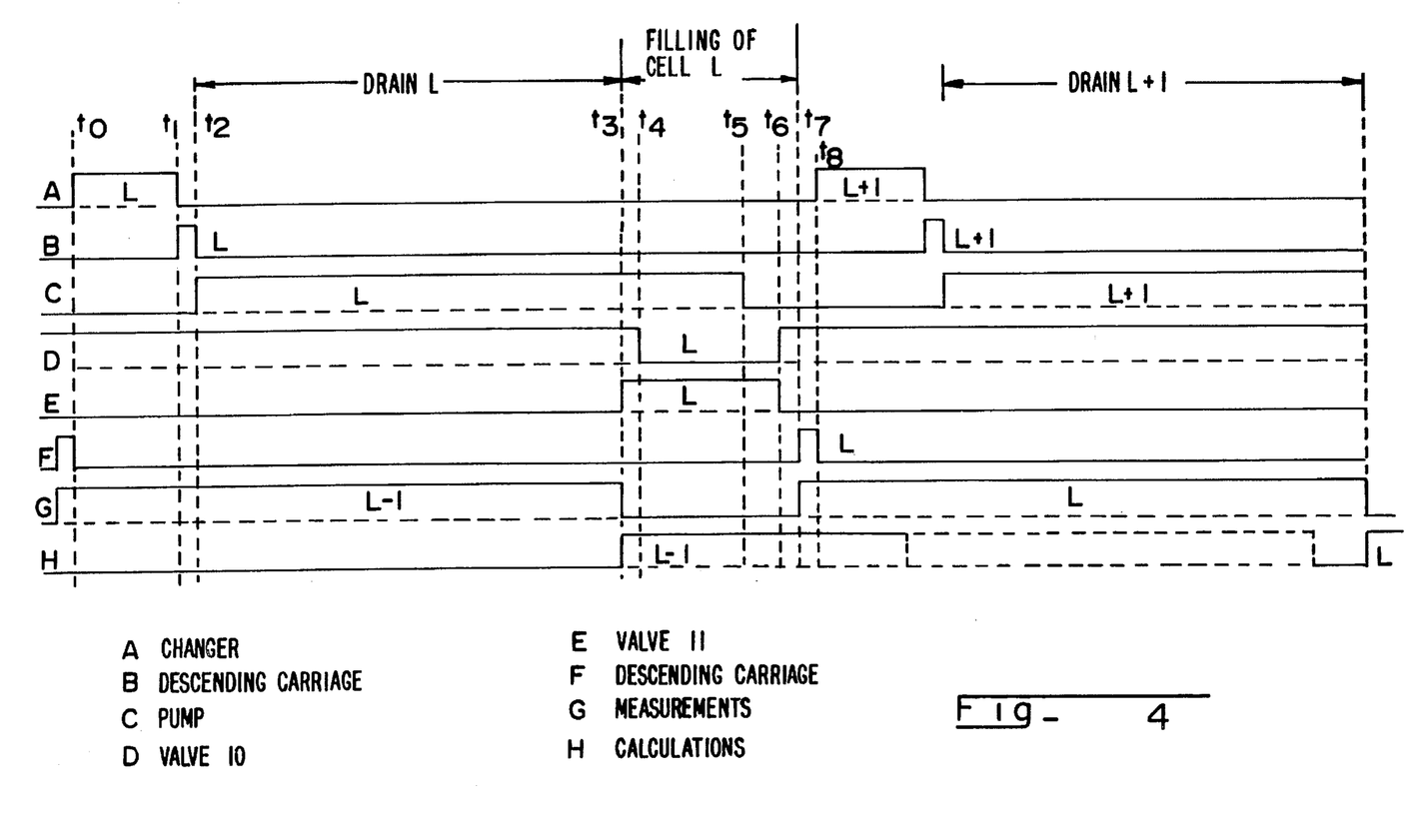
FIG. 4 is a timing diagram.

The U.C.C. control of the movements of the changer 22, the carriage 4 of pump 1, and the valves 10 and 11 are organized according to a cycle extending between a time ($t_1$) and a time ($t_8$); the progress of the cycle is marked by times ($t_1$), ($t_2$), . . . , ($t_8$), the duration $t_2-t_3$ being a draining phase during which the circuit between the pipette and valve 10 is cleaned, and duration $t_3-t_7$ is a filling phase of the cell:

at time ($t_0$), the carriage (4) being in an raised position, the changer advances to place a receptacle, containing a given liquid (L) included in a liquid series to be assayed, . . . , L−1, L, L+1, . . . , to face the pipette; it stops at time ($t_1$), the carriage descends at time ($t_1$) in order to stop in a low position at time ($t_2$), at time ($t_2$) pump 1 turns itself on, with valve 10 open and valve 11 closed; during the draining phase $t_2-t_3$, the liquid cleans the circuit between the pipette and valve 10, at time ($t_3$) valve 11 opens, valve 10 still being open; during a period $t_3-t_4$ the liquid from the receptacle traverses both valves 10 and 11, at time ($t_4$), valve 10 closes, valve 11 still being open; during a period $t_4-t_6$, the liquid is allowed to pass only through valve 11, at time ($t_5$), the pump stops, at time ($t_6$), the valve 10 opens and the valve 11 closes again, at time ($t_7$), the carriage climbs and .stops in the raised position at time ($t_8$), at which time the changer begins a new cycle, at time ($t_7$) and until the end of the draining of the next liquid (L+1), the measurements being undertaken on liquid (L), these measurements on liquid (L) being followed by calculations concerning the same liquid based on the filling phase concerning liquid (L+1); these calculations can be extended until the end of the liquid (L+2) draining phase.

Figure 3:
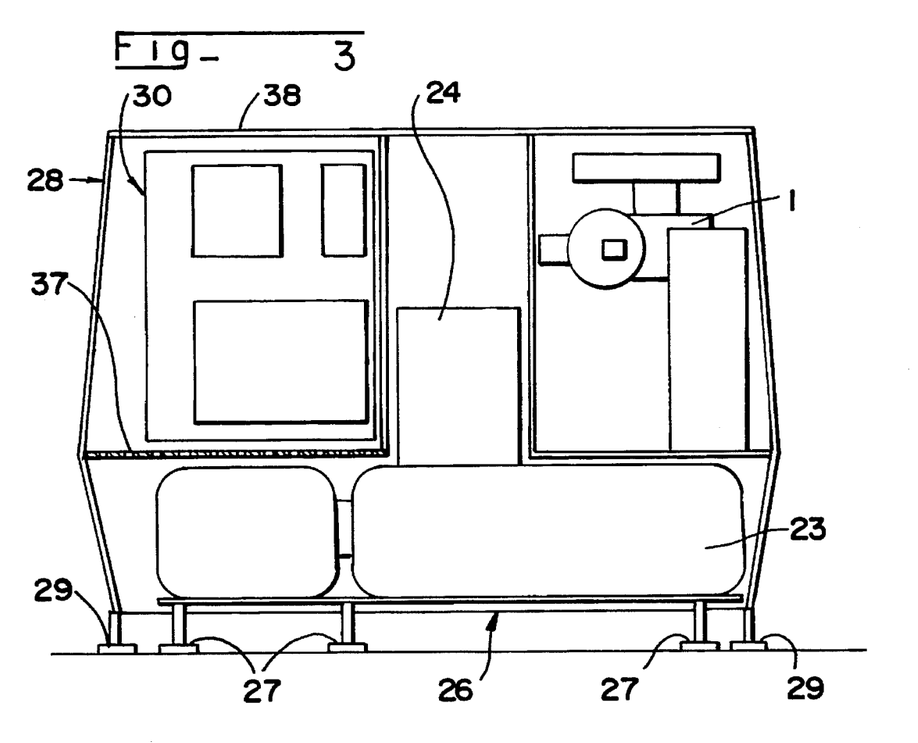
FIG. 3 is a front schematic view of the apparatus showing the mechanical separation between these two portions.

To prevent mechanical vibrations in the measurement container, the apparatus is constructed in two mechanically separated portions:

a first portion 26 constituted by the interferometer 23 and the measurement container 24, this first portion being equipped with legs 27 damping the vibrations, and a second portion 28 straddling the first portion, this second portion also being equipped with legs 29 damping the vibrations, hydrous and electrical connections being obtained between both portions by means of flexible linkage elements.

The pump is fixed onto the second portion by vibration absorption means.

The apparatus is equipped with ventilation means located at the level of its upper wall 38 (not shown).

The calculation and control unit 30 is included in a compartment whose lower wall 37 is permeable, in order to enable the circulation of air forced by the ventilation.

We claim:

1. Method for spectrometric assay of aqueous liquids containing components $X_1, X_2, \ldots, X_n$, to determine their concentration $C_1, C_2, \ldots, C_n$, respectively, comprising:

taking interferometric measurements over an infrared spectrum whose wavelength is 2 to 25 µm through an aqueous liquid sample having a thickness of 10 to 20 µm, at a temperature of 35° to 50° C. with a maximum temperature fluctuation of 0.2° C., and a maximum relative hygrometry of 1%;

determining absorption curves with respect to a matrix; and calculating the concentrations of the components in said aqueous liquid sample.

2. Apparatus for spectrometric assay of aqueous liquids containing components $X_1, X_2, \ldots, X_n$, to determine their concentration $C_1, C_2, \ldots, C_n$, respectively, comprising:

means for taking interferometric measurements over an infrared spectrum whose wavelength is 2 to 25 µm through an aqueous liquid sample having a thickness of 10 to 20 µm, at a temperature of 35° to 50° C. with a maximum temperature fluctuation of 0.2° C., and a maximum relative hygrometry of 1%; and means for determining absorption curves with respect to a matrix and calculating the concentrations of the components in said aqueous liquid sample.

3. Method for spectrometric assay of aqueous liquids containing components $X_1, X_2, \ldots, X_n$, to determine their concentration $C_1, C_2, \ldots, C_n$, respectively, from an infrared spectrum whose wavelength is of 2 to 25 µm (frequencies of 400 to 5,000 $cm^{-1}$), comprising:

sampling at least one water interferogram over an infrared spectrum whose wavelength is 2 to 25 µm (frequencies of 400 to 5,000 $cm^{-1}$) through a water thickness of 10 to 20 µm, at a temperature of 35° to 50° C. with a maximum temperature fluctuation of 0.2° C., and a maximum relative hygrometry of 1

;

calculating, from the water interferogram, a spectrum (So(f)) corresponding to an intensity (Io) traversing the water thickness as a function of frequency (f), (So) being the measured values;

sampling at least one interferogram of an aqueous liquid, for the same thickness and under the same conditions as the water interferogram;

calculating a spectrum (S(f)), corresponding to an intensity (I) traversing the liquid thickness as a function of frequency (f);

determining, from (So(f)) and (S(f)), the absorbency (A(f)) given A(f)=Log (So/S)=Log (Io/I); and determining the concentration of each respective component, based on the absorbency (A(f)) in comparison with previously determined absorbency (A(f)) from reference analyses.

4. The method according to claim 3, comprising determining the concentration ($C_n$) of each component ($X_n$) by taking into consideration a plurality of absorbencies $A(f_1)$, $A(f_2), \ldots, A(f_r)$ according to a standard relation $Cn = a_{n1}A(f_1) + a_{n2}A(f_2) + \ldots , a_{nr}A(f_r) + A_{nk}$, where $A(f_1)$, $A(f_2), \ldots, A(f_r)$ are the absorbency values determined for the liquid at frequencies $f_1, f_2, \ldots, f_r$ and $a_{n1}, a_{n2}, \ldots, a_{nr}$, $a_{nk}$ are correlation constants determined by multiple linear regression based on reference samples with known concentrations and interferometric measurements undertaken on the same samples and corresponding to the same frequencies $f_1, f_2, \ldots, f_r$.

5. The method according to claim 3, wherein the sampling of each interferogram is undertaken at:

a temperature of 37° to 45° C. with a maximum fluctuation of 0.1° C.; and a maximum relative hygrometry of 0.2%.

6. The method according to claim 3, wherein the sampling of each interferogram is undertaken at:

a temperature of 38° to 42° C. with a maximum fluctuation of 0.1° C.

7. Apparatus for assaying of aqueous liquids containing components $X_1, X_2, \ldots, X_n$, to determine their concentration $C_1, C_2, \ldots, C_n$, respectively, by absorbing infrared radiation with a wavelength ranging from 2 to 25 µm, comprising:

an interferometer producing a polychromatic beam interfered with by successive phase shifts obtained around a zero phase shift;

a calculation and control unit for receiving and sending signals;

a measurement container containing:

means for detecting temperature and outputting a significant signal transmitted to said calculation and control unit, means for heating controlled by said calculation and control unit in order to maintain a temperature inside of said measurement container at a value between 35° and 50° C. with a maximum fluctuation of 0.2° C., means for limiting relative humidity to a maximum value of 1%, a cell comprising a flattened shape and an internal spacing of 10 to 20 µm capable of being filled with liquid to be assayed, a photosensitive detector for receiving an interfered beam after traversing said cell and outputting consistent signals for each phase shift to said calculation and control unit for calculating:

a spectrum (S(f)) corresponding to an intensity (I) traversing the liquid thickness transmitted as a function of the frequency (f), an absorbency A(f)=Log (So/S)=Log Io/I where (Io) is an intensity traversing a thickness of water as a function of frequency (f), and the concentrations $C_1, C_2, \ldots, C_n$, from the absorbency and previously determined by absorbency for reference analyses.

8. The apparatus according to claim 7, comprising a pipette carried by a vertically movable carriage for aspirating liquid from a receptacle.

9. The apparatus according to claim 8, further comprising a pump downstream from said pipette.

10. Apparatus according to claim 9, comprising two mechanically separated portions:
- a first portion comprising said interferometer and said measurement container, said first portion being equipped with legs for damping vibrations;
- a second portion straddling said first portion, said second portion also comprising legs for damping vibrations; and
- flexible linkage elements providing hydrous and electrical connections between both portions.

11. Apparatus according to claim 10, wherein said pump is fixed onto said second portion by vibration absorption elements.

12. Apparatus according to claim 9, comprising:
- a first heat sensor for performing a first temperature regulation step located in a vicinity of said pump for detecting a first temperature ($T_1$,) of liquid to be introduced into said measurement container, and outputting a significant signal of the first temperature to said calculation and control unit, and a first heating means controlled by said calculation and control unit for maintaining the first temperature of the liquid intended for analysis at a temperature ($T_1$);
- wherein said means for detecting temperature comprise a second heat sensor for performing a second temperature regulation step located in said measurement container for measuring a second temperature ($T_2$,) of an ambient environment of said measurement container, and outputting a thermal signal of the second temperature to said calculation and control unit, and said means for heating comprise a second heating means controlled by said calculation and control unit for maintaining the second temperature of the ambient environment at a temperature ($T_2$), where $T_2 - T_1 = +0.5°$ C.; and
- a third heat sensor for performing a third temperature regulation step, affixed to said cell, for measuring a third temperature ($T_3$,), and outputting a significant signal of the third temperature to said calculation and control unit, and a third heating means controlled by said calculation and control unit for maintaining said cell at a temperature ($T_3$), where $T_3 - T_2 = +0.5°$ C.

13. Apparatus according to claim 12, wherein
said first heat sensor is located on said pump and said first heating means comprise a heating collar surrounding said pump;
said second heat sensor is located in the ambient environment of said measurement container, and said second heating means comprises a heating block located on a base of said measurement container; and
said third heat sensor is affixed to said cell, and said third heating means comprise a heating belt surrounding said cell.

14. The apparatus according to claim 9, further comprising a filter downstream of said pump, said filter comprising an inlet, a first outlet and a second outlet, a first controlled valve for controlling flow through said first outlet, and a second controlled valve connected to said cell for controlling flow through said cell.

15. The apparatus according to claim 14, wherein said cell comprises a lowest level and a highest level, an inlet is located at said lowest level, and an outlet is located at said highest level.

16. The apparatus according to claim 15, wherein said outlet of said cell and said first outlet of said filter are connected to a receptacle.

17. The apparatus according to claim 15, wherein said outlet of said cell and said first outlet of said filter are connected to a drain channel.

18. Apparatus according to claim 7, comprising:
- a carriage vertically movable between a low position and a raised position;
- a pipette carried by said carriage; and
- a changer for carrying receptacles containing liquid samples to be analyzed.

19. The apparatus according to claim 18, further comprising a filter downstream of said pump, said filter comprising an inlet, a first outlet and a second outlet, a first controlled valve for controlling flow through said first outlet, and a second controlled valve connected to said cell for controlling flow through said cell.

20. Apparatus according to claim 19, wherein said calculation and control unit controls movement of said changer, said carriage and said pump, and said first controlled valve and said second controlled valve is organized according to a cycle extending between a time ($t_1$) and a time ($t_8$), with progress of the cycle being marked by times ($t_1$), ($t_2$), . . . , ($t_8$), the duration $t_2$–$t_3$ being a draining phase during which a circuit between said pipette and said first controlled valve is cleaned, and duration $t_3$–$t_7$ is a filling phase of said cell, said cycle comprising:
- at time ($t_o$), said carriage is in the raised position, said changer advances to place a receptacle containing a given liquid (L) included in a series of liquid to be assayed, . . . , L–1, L, L+I, to face said pipette; and said changer stops at time ($t_1$),
- said carriage descends at time ($t_1$) to stop at the low position at time ($t_2$),
- at time ($t_2$), said pump turns on, said first controlled valve is open and said second controlled valve is closed; during the draining phase $t_2$–$t_3$, liquid cleans the circuit between said pipette and said first controlled valve,
- at time ($t_3$), said second controlled valve opens, the first controlled valve remains open; during a period $t_3$–$t_4$, liquid from the receptacle traverses both said first controlled valve and said second controlled valve,
- at time ($t_4$), the first controlled valve closes, said second controlled valve remains open; during a period $t_4$–$t_6$, the liquid is allowed to pass only through said second controlled valve,
- at time ($t_5$), said pump stops,
- at time ($t_6$), said first controlled valve opens and said second controlled valve closes again,
- at time ($t_7$), said carriage is raised and stops in the raised position at time ($t_8$), at which time said changer begins a new cycle,
- at time ($t_7$) and until the end of draining of the next liquid (L+1), measurements being undertaken on liquid (L) are followed by calculations concerning the same liquid based on the filling phase concerning liquid (L+1), such calculations being extendable until an end of a draining phase concerning the liquid (L+2).

21. Apparatus according to claim 18, comprising an agitator associated with said carriage, said agitator being stopped in the raised position and in operation in the low position.

22. Apparatus according to claim 21, wherein said pipette and said agitator are spaced a predetermined distance, and a spacing between two successive receptacles on said changer is equal to said predetermined distance so that in the low position said pipette is located in one receptacle and said agitator is located in a next receptacle.

23. Apparatus according to claim 18, wherein said changer comprises an endless band.

* * * * *